US010172637B2

(12) United States Patent
Caruso

(10) Patent No.: US 10,172,637 B2
(45) Date of Patent: Jan. 8, 2019

(54) DISSECTOR DEVICE

(71) Applicant: AB MEDICA HOLDING S.P.A., Milan (MI) (IT)

(72) Inventor: Carlo Caruso, Rome (IT)

(73) Assignee: AB MEDICA HOLDING S.P.A., Milano (MI) (IT)

( * ) Notice: Subject to any disclaimer, the term of this patent is extended or adjusted under 35 U.S.C. 154(b) by 89 days.

(21) Appl. No.: 15/326,537

(22) PCT Filed: Jul. 21, 2015

(86) PCT No.: PCT/IB2015/055510
§ 371 (c)(1),
(2) Date: Jan. 16, 2017

(87) PCT Pub. No.: WO2016/012936
PCT Pub. Date: Jan. 28, 2016

(65) Prior Publication Data
US 2017/0209165 A1    Jul. 27, 2017

(30) Foreign Application Priority Data
Jul. 21, 2014    (IT) .................. 102014902280494

(51) Int. Cl.
*A61B 17/00*    (2006.01)
*A61B 17/3203*    (2006.01)
(Continued)

(52) U.S. Cl.
CPC ........ *A61B 17/3203* (2013.01); *A61B 17/295* (2013.01); *A61B 17/3201* (2013.01);
(Continued)

(58) Field of Classification Search
CPC . A61B 17/3201; A61B 17/3203; A61B 17/29; A61B 17/295; A61B 2017/2926;
(Continued)

(56) References Cited

U.S. PATENT DOCUMENTS 5,707,382 A    1/1998    Sierocuk et al.
6,001,120 A    12/1999   Levin
(Continued)

FOREIGN PATENT DOCUMENTS

DE          3715418 A1    11/1987
DE    102006027873 A1     1/2008
(Continued)

OTHER PUBLICATIONS

International Search Report and Written Opinion for International Application No. PCT/IB2015/055510 (dated Nov. 13, 2015) (12 Pages).

*Primary Examiner* — Melanie R Tyson
(74) *Attorney, Agent, or Firm* — Lucas & Mercanti, LLP

(57) ABSTRACT

A dissector device having a rod-shaped hollow member, an expandable element with a pair of jaws arranged at a distal end of the rod-shaped member and a grip arranged at a proximal end of the rod-shaped member is provided. The dissector device has dispensing assembly for dispensing a fluid under pressure and has feeding channels and a dispensing channel associated with the jaws of the expandable element. The dispensing channel being has an outlet arranged proximate to or at the free end of the jaw. The feeding channels are arranged in fluid communication with a cavity of the rod-shaped member, whereby a fluid under pressure is fed throughout the cavity of the rod-shaped member in an operating condition of the dissector device.

10 Claims, 3 Drawing Sheets

(51) Int. Cl.
*A61B 17/295* (2006.01)
*A61B 17/3201* (2006.01)
*A61B 17/32* (2006.01)

(52) U.S. Cl.
CPC ............ *A61B 2017/00353* (2013.01); *A61B 2017/32035* (2013.01); *A61B 2017/320044* (2013.01); *A61B 2217/007* (2013.01)

(58) Field of Classification Search
CPC .......... A61B 2017/32032; A61B 2017/32035; A61B 2017/320044
USPC ................................................ 606/174, 190
See application file for complete search history.

(56) References Cited

U.S. PATENT DOCUMENTS

| | | |
|---|---|---|
| 2002/0183738 A1 | 12/2002 | Chee et al. |
| 2009/0076505 A1 | 3/2009 | Arts |
| 2010/0069903 A1 | 3/2010 | Allen, IV et al. |
| 2014/0094838 A1 | 4/2014 | Neuman et al. |

FOREIGN PATENT DOCUMENTS

| | | |
|---|---|---|
| DE | 102011086032 A1 | 5/2012 |
| WO | 9639953 A1 | 12/1996 |
| WO | 9902089 A1 | 1/1999 |

DISSECTOR DEVICE

CROSS-REFERENCE TO RELATED APPLICATIONS

This application is a 371 of PCT/IB2015/055510, filed Jul. 21, 2015, which claims the benefit of Italian Patent Application No. 102014902280494, filed Jul. 21, 2014.

FIELD OF THE INVENTION

The present invention generally relates to laparoscopic surgical instruments and in particular to a dissector device for dissecting human or animal tissues without cutting them.

BACKGROUND OF THE INVENTION

Surgical procedures often require dissection and displacement of tissues so as to allow access to the anatomical structures to be subjected to an intervention. Dissection of tissues is more and more performed without cutting them and in a substantially atraumatic way by way of special dissector devices.

Such dissector devices typically comprise blunt dissecting elements, such as pairs of jaws, spatulas and the like, which are made to slide along the natural cleavage planes of the tissues to be separated so as to exert a detachment action therebetween.

The publication U.S. Pat. No. 6,001,120 A e.g. discloses a dissector device comprising a pair of levers hinged to each other at an intermediate position thereof. At the distal ends of the levers curved beaks are arranged, while at the proximal ends of the levers slotted grips similar to those of a common scissor are provided so as to allow a surgeon to handle the device with the fingers of a hand. By moving the handles close to or away from each other as it happens with scissors, the curved beaks may be brought close to or away from each other, respectively. Detachment and separation of the tissues, i.e. their dissection, is performed by moving the beaks away from each other when they are suitably arranged between the cleavage planes of the tissues.

The publication US 2014/0094838 A1 discloses a dissector device comprising a rod-shaped element at the distal end of which a pair of articulated beaks is arranged. These beaks may be operated through a kinematic chain restrained to a control lever pivoted at the proximal end of the rod-shaped element. Also in this case detachment of the tissues occurs by moving the beaks away from each other. The provision of a rod-shaped element is advantageous, because it allows a surgeon to operate on tissues from a remote position with respect to the site of the intervention, as it typically occurs in laparoscopic procedures.

The publication U.S. Pat. No. 5,707,382 A discloses a dissector device comprising a rod-shaped element at the distal end of which an expandable balloon is arranged. The expansion of the balloon between the cleavage planes of the tissues causes detachment and separation similarly to what occurs by moving the beaks of the dissectors devices mentioned above away from each other.

The international publication WO 99/02089 A1 discloses a dissector device comprising a rod-shaped element whose distal end comprises apertures configured to deliver a flow of pressurized gas, for example carbon dioxide. In this case tissue dissection is not obtained mechanically by pressing and/or operating expandable members against the tissues, but due to the dynamic action of a fluid medium injected therebetween.

Another dissector device of this type is disclosed in the publication US 2009/0076505 A1. In this case a gas supplied from a distal end of a rod-shaped element is ionized by way of an active electrode, thus allowing to cause not only detachment and separation of the tissues, but also to obtain a drying and coagulation effect.

The publication DE 10 2006 027 873 A1 discloses a dissector device comprising a rod-shaped element, an expandable element consisting of a pair of beaks or jaws arranged at a distal end of the rod-shaped element, wherein the jaws are hinged to each other and restrained at the distal end of the rod-shaped element by a pin and are operatively connected to a control rod that is slidably fitter in the rod-shaped element. The dissector device further comprises a dispensing assembly for dispensing a pressurized fluid, in particular a saline solution, comprising a feeding channel a dispensing aperture of which is arranged close to a fixed jaw of the expandable element.

A structurally similar device is disclosed in the publication DE 10 2011 086 032 A1.

SUMMARY OF THE INVENTION

Despite the availability of dissector devices of different types, there is still the need to find improved solutions that facilitate and simplify the activity of a surgeon, as well as the need to reduce surgical intervention and healing times, which is an object of the present invention.

Said object is achieved with a dissector device whose main features are specified in the independent claim 1. Preferred features of the present invention are object of the dependent claims.

An idea of solution underlying the invention is to combine the mechanical separation action of expandable elements with the dynamic separation action caused by the flow of a pressurized fluid. To this aim, the dissector device comprises a rod-shaped element at the distal end of which an expandable element comprising a pair of jaws hinged to each other is arranged. The dissector device is also provided with a dispensing assembly configured for the feeding of a pressurized fluid from a remote source to at least one dispensing aperture associated with the expandable element, in particular arranged close to or at its free end. The pressurized fluid is fed through a series of channels arranged in fluid communication with a hollow rod-shaped element, wherein a driving rod of the jaws of the expandable element is fitted.

The structure of the dissector device is therefore much simpler and smaller than those characterizing known dissector devices, because the cavity of the rod-shaped element serves not only as a guide for the driving rod, but also as a channel for feeding the pressurized fluid towards the expandable element.

The channels of the dispensing assembly may be advantageously integrated in a grip of the dissector device to which the rod-shaped element is connected, thus improving ergonomics of the dissector device.

According to a further aspect of the invention, the inner edges of the jaws of the expandable element, opposite to the edges intended to contact the tissues, may be sharp, so as to allow to use the expandable element of the dissector device as a scissor. Thanks to these features, the dissector device according to the invention is a very versatile instrument, because it allows a surgeon to perform dissections also in the traditional way, if this is necessary.

Different configurations of the inner edges of the jaws, such as e.g. knurled and the like, may be envisioned as well so as to further improve versatility of the dissector device.

BRIEF DESCRIPTION OF THE DRAWINGS

Further advantages and features of the dissector device according to the present invention will become clear to those skilled in the art from the following detailed and non-limiting description of embodiments thereof, with reference to the accompanying drawings wherein.

DETAILED DESCRIPTION OF THE INVENTION

Figure 1:
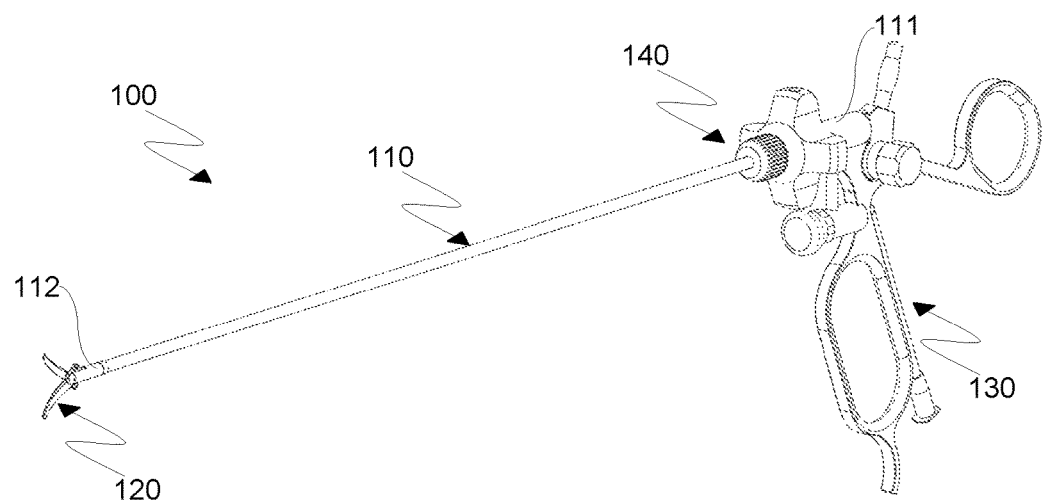
FIG. 1 is a perspective view showing a dissector device according to the invention.
Figure 2:
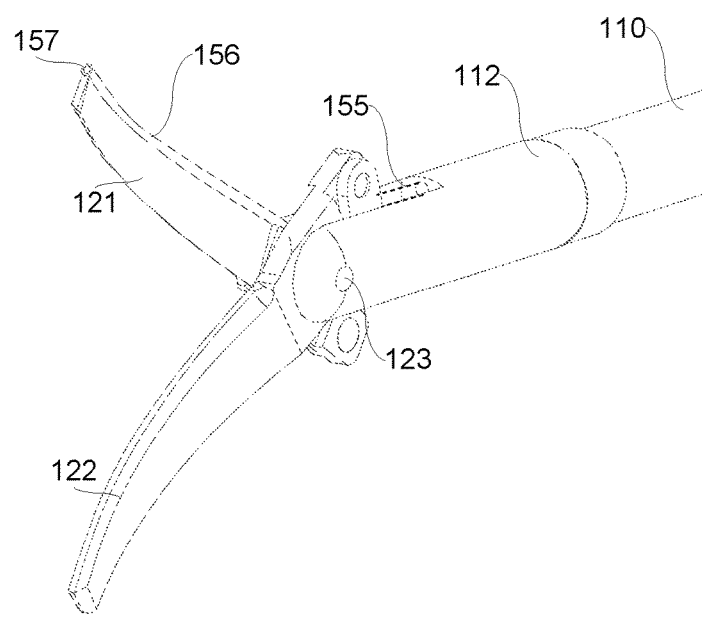
FIG. 2 is a detailed view showing an expandable element of the dissector device of FIG. 1.

Referring to FIGS. 1 and 2, a dissector device according to the invention is generally indicated by the reference number 100.

The dissector device 100 comprises a rod-shaped element 110 that has a proximal end 111 intended to be held by a surgeon and a distal end 112, opposite the proximal end 111, intended to be introduced into the body of a patient, typically through a trocar, so as to allow to carry out dissections during a surgical intervention.

The device 100 comprises an expandable element 120 arranged at the distal end 112 of the rod-shaped element 110 and configured for blunt dissection of tissues. The expandable element comprises a pair of beaks or jaws 121, 122 that are hinged to each other and restrained at the distal end 112 of the rod-shaped element 110 by way of a pin 123.

The device 100 also comprises a grip 130 connected to the proximal end 111 of the rod-shaped element 110. The grip 130 comprises a fixed member 131 and a driving lever 132 pivoted on the fixed member 131. The grip 130 may also comprise an electrical connection 133 configured to allow electrical connection of the jaws 121, 122 of the expandable element 120 to a power source so as to carry out electro-coagulation procedures.

Both the fixed member 131 that the driving lever 132 comprise slotted portions allowing a surgeon to insert the fingers of a hand so as to facilitate maneuvering of the dissector device. The slotted portion of the fixed member 131 is e.g. configured to receive three fingers of a hand, in particular the middle, ring and little fingers, while the slotted portion of the driving lever 132 is e.g. configured to receive the thumb.

The connection between the handle 130 and the rod-shaped element 110 is preferably of a removable type and may be achieved in a known manner e.g. by way of a coupling 140 rotatably restrained to the grip 130. This configuration allows to disassemble the rod-shaped element 110 and the components associated therewith after each surgical procedure, for the purpose of washing and sterilization or complete replacement.

The coupling 140 is cross-shaped so as to allow a surgeon to rotate it by using the forefinger of the same hand handling the device 100. The provision of a rotatable connection allows to perform rotations rod-shaped element 110 without changing the position of the device relative to the body of the patient, which is particularly important in laparoscopic procedures, that are characterized by a rather small maneuvering space.

Figure 3:
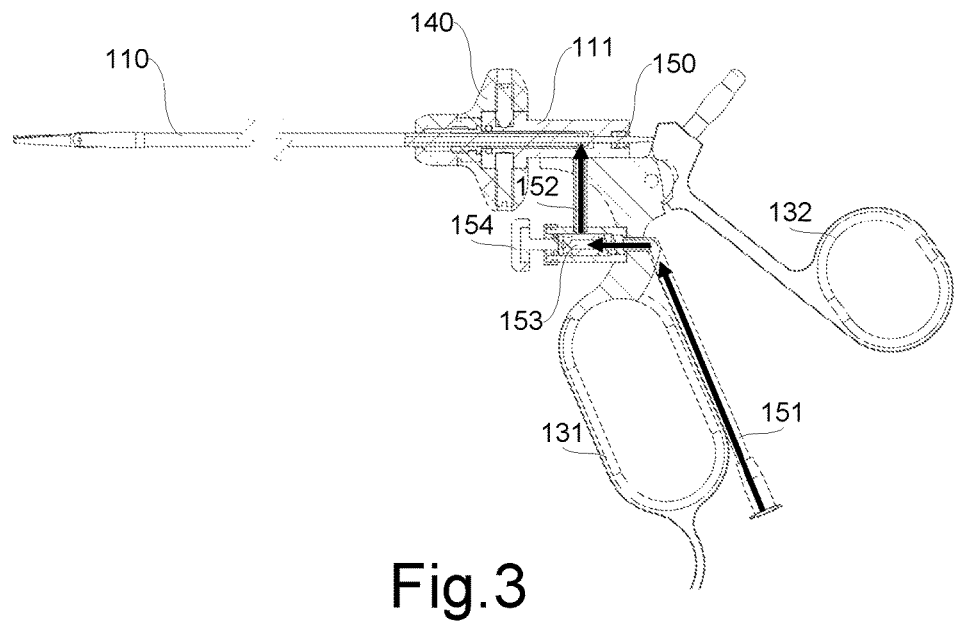
FIG. 3 is a partial view in longitudinal section of the dissector device of FIG. 1 that shows some details of its grip and of the rod-shaped element connected thereto.

As shown in FIG. 3, the driving lever 132 is restrained to a rod 150 slidably fitted into a cavity 113 of the rod-shaped element 110 and operatively connected to the jaws 121, 122.

The driving lever 132, the rod 150 and the restraining means connecting the rod 150 to the jaws 121, 122 form a kinematic chain, whose configuration is such that, by moving the driving lever 132 away from the fixed member 131 of the grip 130, the rod 150 is moved towards the distal end 112 of the rod-shaped element 110, thus causing the jaws 121, 122 to move away from each other, i.e. expansion of the expandable element. Opening of the jaws 121, 122 determines detachment of the tissues in contact with them, which allows to obtain their dissection along the cleavage planes without resorting to cuts.

By approaching the lever 132 to the fixed member 131 of the grip 130, the rod 150 is instead moved towards the proximal end 111 of the rod-shaped element 110, thus causing the jaws 121, 122 to move close to each other, i.e. closing of the expandable element.

Figure 5:
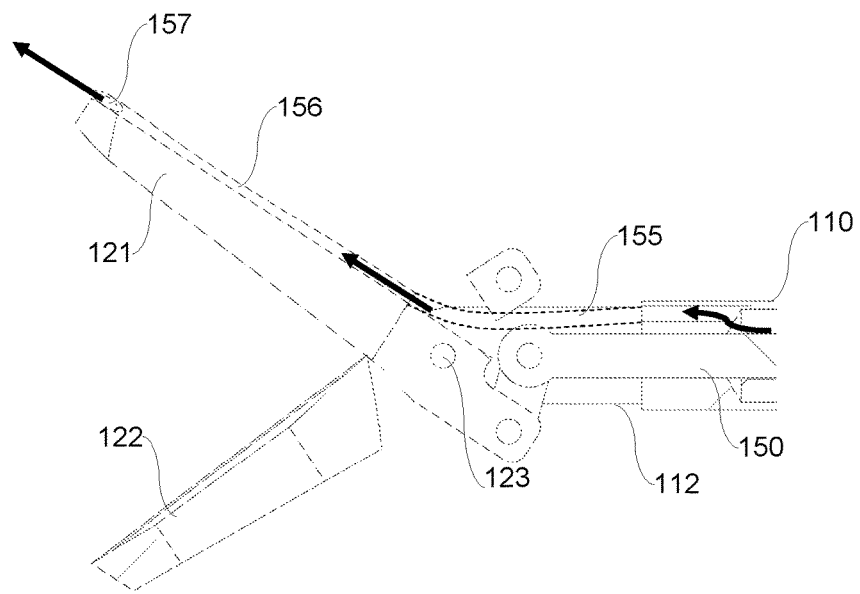
FIG. 5 is a partial view in longitudinal section of the device of FIG. 1 that shows the expandable element of the device of FIG. 1 according to an embodiment of the invention.

As shown in FIG. 5, the restraining means between the rod 150 and the jaws 121, 122 may for example be configured as a deformable parallelogram in which two connecting arms are pivoted at the free end of the rod 150, the two connecting arms being in turn pivoted at respective portions of the jaws 121, 122 that extend from the pin 123 away from their free ends.

Figure 6:
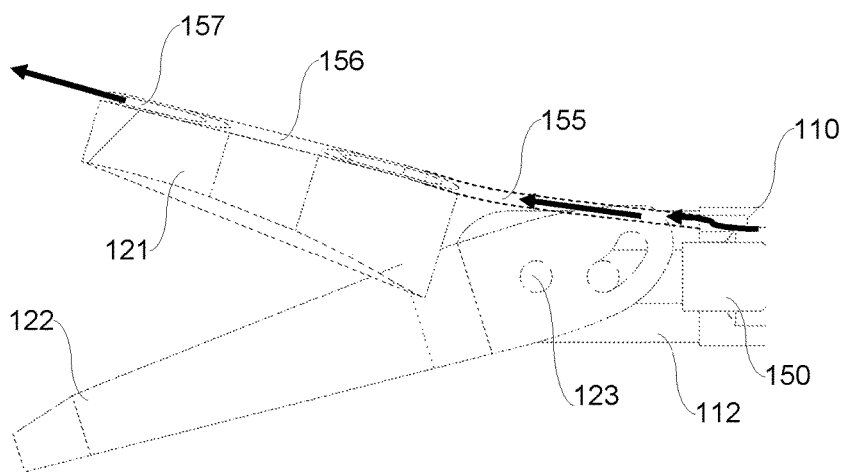
FIG. 6 is a partial view in longitudinal section of the device of FIG. 1 that shows the expandable element of the device of FIG. 1 according to an alternative embodiment of the invention.

Alternatively, as shown in FIG. 6, the restraining means between the rod 150 and the jaws 121, 122 may be configured as a cam-follower system wherein on each jaw 121, 122 a cam is formed, for example in the form of an arcuate slot, and the follower is e.g. a pin restrained at the free end of the rod 150.

According to the invention, the dissector device 100 also comprises a dispensing assembly configured to supply a pressurized fluid, in particular a gas such e.g. as carbon dioxide, from a remote source to at least one dispensing aperture associated to the expandable element 120.

The dispensing assembly comprises a series of channels that extend from the grip 130 toward the expandable element 120 passing through the rod-shaped element 110, as it will be described in detail below.

Still with reference to FIG. 3, according to an embodiment of the invention a first and a second supply channel 151, 152 are associated to the fixed member 131 of the grip 130. The first channel 151 is configured for connection to a remote fluid source (not shown) and stretches out along the slotted portion of the fixed member 131, while the second channel 152 is arranged in fluid communication with the first channel 151 and the cavity 113 of the rod-shaped element 110, wherein the rod 150 is slidably fitted. The second channel 152 is e.g. connected to the rod-shaped element 110 at its proximal end 111.

Thanks to this configuration, the passage of a pressurized fluid occurs coaxially to the rod 150 directly through the hollow rod-shaped element 110, without resorting to respective inner or outer channels as it happens in known dissector devices. The main advantage of this configuration is that the structure of the dissector device is less complex and cumbersome than the structure of known devices. This structural simplification also results in a reduction of the manufacturing costs of the dissector device.

Still with reference to FIG. 3, between the two feeding channels 151, 152 there may be advantageously arranged a flow regulating valve 153. Adjustment of the flow may be advantageously obtained by way of a driving button 154 associated with the valve 153, the button being operable by the forefinger of the hand holding the dissector device 100.

Figure 4:
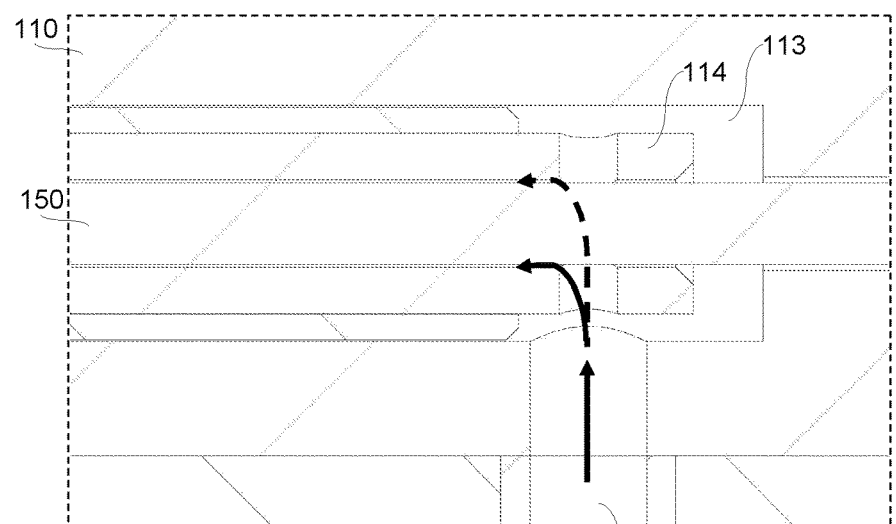
FIG. 4 shows a detail IV of FIG. 3.

As shown in the detail of FIG. 4, a tubular member 114 is preferably fitted in the cavity 113 of the rod-shaped element 110. The tubular member is arranged coaxially to the rod 150. The tubular member 114 is configured so as to define a radial clearance with the rod 150, which defines a cylindrical sleeve passage or duct adapted to allow a flow of pressurized fluid through the rod-shaped element 110 from the proximal end 111 to the distal end 112.

Compared to the passage of the pressurized fluid through the whole cavity 113 of the rod-shaped element 110, this configuration offers the advantage of a better control of the flow, because the surface areas of the fluid passages through the feeding channels 151, 152 and the sleeve duct defined between the tubular element 114 and the rod 150 are mutually comparable and thus do not generate remarkable head losses between the different channels, nor turbulent flow conditions, which may adversely affect operation of the dissector device 100 during a surgical procedure.

At the distal end 112 of the rod-shaped element 110 a third supply channel 155 (shown in dotted line in FIGS. 5 and 6) is tightly connected, the third supply channel being in turn tightly connected to at least one dispensing channel 156 associated with the expandable element 120. In order to allow relative movements between the expandable element 120 and the rod-shaped element 110, the third supply channel 155 is advantageously a flexible tube.

In the embodiment shown in FIGS. 2, 5 and 6, the dissector device 100 comprises a single dispensing channel 156 arranged and restrained along an outer edge of any one of the jaws 121, 122 of the expandable element 120, for example, jaw 121. It will be understood that the dissector device 100 might also comprise two dispensing channels, respectively associated to each jaw 121, 122. In this case there could be used a third and a fourth feeding channels connected at the distal end 112 of the rod-shaped element 110, or a single feeding channel provided with a bifurcation so as to bring the fluid to each delivery channel associated to the jaws 121, 122.

In the frame of the present invention, the wording "outer edges" referred to the jaws indicated the edges of the jaws intended to contact the tissues to be separated. Consequently, "inner edges" are the edges of the jaws facing each other.

At the free end of the dispensing channel 156, or close thereto, there is a dispensing aperture 157 arranged at the free end of the same jaw 121.

Arrangement of the aperture 157 at the free end of the jaw 121, and hence of the expandable element 120, is advantageous because it allows to direct streams of pressurized fluid from the free end of the blunt dissector device 100 to the tissues to be separated upon its insertion in the site of the surgical intervention, thus facilitating the subsequent opening phase of the jaws 121, 122, and more generally the expansion of the expandable element 120.

FIGS. 3 to 6 schematically show the path of the pressurized fluid by way of arrows.

In order to carry out a dissection, the dissector device 100 according to the invention is brought into the operative site with the expandable element 120 in the closed configuration. The expandable element 120 is approached or brought into contact with the cleavage planes of the tissues to be separated. A small incision is made in the lower edge of the area where dissection has to be performed and a flow of pressurized fluid is delivered against the tissues. This generates a detachment action of the tissues. The result is a sort of bubble that is generated upon dissection, which makes the dissection atraumatic and free from bleeding because it does not occur in vascularized areas. During this operation step the driving lever 132 is operated so as to progressively open the jaws 121, 122 of the expandable element 120, thus synergistically contributing to the detachment of tissues started by the flow of pressurized fluid.

In this way a quicker and above all safer dissection of the tissues is obtained, thanks to the spontaneous detachment of the tissues along their cleavage planes and to the fact that the detachment areas are not vascularized.

According to an embodiment of the invention, the dispensing channel 156 may advantageously comprise further dispensing apertures (not shown) formed in its mantle in a radial direction and arranged so as to enable dispensing of pressurized fluid not only towards the free end of the expandable element 120 of the dissector device 100, but also from its sides, thus offering the advantage of synergistically contributing to the mechanical separating action of the tissues made carried out by the expandable element 120 not only at the beginning of the procedure, but also during the whole expansion phase.

According to an alternative embodiment of the invention, the at least one dispensing channel 156 can be formed integrally with the expandable element 120, in particular inside any one of the jaws 121, 122, or in both of them, so that the dispensing aperture 157 is placed at the free end of jaw 121 and/or 122.

Also in this case, the dispensing channel 156 may advantageously comprise further delivery apertures (not shown), for example formed along the outer edge of the jaw 121 or at its sides.

According to a further aspect of the invention, the jaws 121, 122 of the expandable element 120 may advantageously be provided with sharp inner edges, such as shown in FIG. 6, so that the jaws 121, 122 may be used not only as blunt elements for the separation of the tissues in the opening movement of the expandable element 120, but also as cutting elements when carrying out the opposite, closing movement of the expandable element 120. Knurled or, more generally, textured surfaces may be envisioned as well so as to improve versatility of use of the jaws 121, 122 of the expandable element 120, and hence of the whole dissector device.

The present invention has hereto been described with reference to preferred embodiments thereof. It is to be understood that there may be other embodiments relating to the same inventive idea, as defined by the scope of protection of the claims set forth below.

The invention claimed is:

1. A dissector device comprising a rod-shaped hollow member, an expandable element consisting of a pair of jaws arranged at a distal end of the rod-shaped member and a grip arranged at a proximal end of the rod-shaped member, wherein said jaws are hinged to each other and restrained to the distal end of the rod-shaped member by way of a pin and wherein said grip comprises a fixed element and a driving lever pivoted on said fixed element, said driving lever being restrained to a rod slidably fitted in the rod-shaped member and operably connected to the jaws, said dissector device further comprising a dispensing assembly for dispensing a pressurized fluid, said dispensing assembly comprising feeding channels and a dispensing channel associated with a jaw of the pair of jaws of the expandable element, said dispensing channel being provided with a dispensing outlet arranged proximate to or at a free end of said jaw, wherein said feeding channels are arranged in fluid communication with a cavity of the rod-shaped member wherein the rod is slidably fitted, whereby a pressurized fluid is fed throughout the cavity of the rod-shaped member in an operating condition of the dissector device, wherein a tubular member is fitted in the cavity of the rod-shaped member, said tubular member being arranged coaxially to the rod, and wherein a radial play is present between the rod and the tubular member, said radial play defining a cylindrical sleeve duct suitable to allow feeding of a fluid under pressure throughout the rod-shaped member.

2. The dissector device according to claim 1, wherein the feeding channels comprise a first and a second supply channel associated to the fixed element of the grip, and wherein said first supply channel is configured for connection to a remote fluid supply source and said second supply channel is arranged in fluid communication with the cavity of the rod-shaped member.

3. The dissector device according to claim 2, said dissector device further comprising a flow regulation valve, said flow regulation valve being arranged between the first and the second supply channels.

4. The dissector device according to claim 3, wherein said flow regulation valve is provided with a driving button.

5. The dissector device according to claim 2, wherein the feeding channels further comprise a third supply channel fluid-tightly connected to the distal end of the rod-shaped member, said third supply channel being in turn fluid-tightly connected to said dispensing channel.

6. The dissector device according to claim 1, wherein said dispensing channel is arranged along an outer edge of any one jaw of the pair of jaws of the expandable element and restrained thereto.

7. The dissector device according to claim 6, wherein said dispensing channel is provided with a dispensing aperture arranged proximate to or at the free end of the jaw and with further dispensing apertures formed in its mantle in the radial direction.

8. The dissector device according to claim 1, wherein said dispensing channel is formed inside the jaw of the expandable element.

9. The dissector device according to claim 8, wherein said dispensing channel is provided with a dispensing aperture arranged proximate to the free end of the jaw and with further dispensing apertures formed in its outer edge.

10. The dissector device according to claim 1, wherein the jaws of the expandable element are provided with sharp inner edges.

* * * * *